US008637587B2

(12) United States Patent
Xu et al.

(10) Patent No.: US 8,637,587 B2
(45) Date of Patent: Jan. 28, 2014

(54) RELEASE AGENT PARTITION CONTROL IN IMPRINT LITHOGRAPHY

(75) Inventors: Frank Y. Xu, Round Rock, TX (US); Weijun Liu, Cedar Park, TX (US)

(73) Assignee: Molecular Imprints, Inc., Austin, TX (US)

( * ) Notice: Subject to any disclaimer, the term of this patent is extended or adjusted under 35 U.S.C. 154(b) by 0 days.

(21) Appl. No.: 13/226,635

(22) Filed: Sep. 7, 2011

(65) Prior Publication Data

US 2011/0319516 A1 Dec. 29, 2011

Related U.S. Application Data

(63) Continuation of application No. 12/612,527, filed on Nov. 4, 2009.

(60) Provisional application No. 61/111,509, filed on Nov. 5, 2008.

(51) Int. Cl.
C08F 2/50 (2006.01)

(52) U.S. Cl.
USPC .............. 522/131; 522/74; 522/71; 522/75; 522/78; 522/83; 522/113; 522/114; 522/129; 522/130; 522/182; 522/178; 264/293; 264/264; 264/338; 264/300; 264/296

(58) Field of Classification Search
USPC .......... 264/293, 338, 364, 300, 296, 200–227, 264/264; 522/71, 74, 75, 78, 79, 83, 113, 522/114, 129, 130, 131, 178, 182
See application file for complete search history.

(56) References Cited

U.S. PATENT DOCUMENTS

| | | |
|---|---|---|
| 3,403,122 A | 9/1968 | Sherman et al. |
| 3,787,351 A | 1/1974 | Olson |
| 3,810,874 A | 5/1974 | Mitsch et al. |
| 4,303,761 A | 12/1981 | Apotheker |
| 4,585,829 A | 4/1986 | Kuo et al. |
| 4,614,667 A | 9/1986 | Larson et al. |
| 4,803,145 A | 2/1989 | Suzuki et al. |
| 4,835,084 A | 5/1989 | Nair et al. |
| 4,845,008 A | 7/1989 | Nishioka |
| 5,298,556 A | 3/1994 | Stephens |
| 5,380,644 A | 1/1995 | Yonkoski et al. |
| 5,389,696 A | 2/1995 | Dempsey et al. |
| 5,397,669 A | 3/1995 | Rao |
| 5,462,700 A | 10/1995 | Beeson et al. |
| 5,525,150 A | 6/1996 | Yamana et al. |
| 5,542,978 A | 8/1996 | Kindt-Larsen et al. |
| 5,569,691 A | 10/1996 | Guggenberger et al. |
| 5,629,128 A | 5/1997 | Shirakawa et al. |
| 5,631,314 A | 5/1997 | Wakiya et al. |
| 5,747,234 A | 5/1998 | Wexler et al. |
| 5,772,905 A | 6/1998 | Chou |
| 5,837,314 A | 11/1998 | Beaton et al. |
| 5,969,063 A | 10/1999 | Parker et al. |
| 6,054,034 A | 4/2000 | Soane et al. |
| 6,093,455 A | 7/2000 | Kamen et al. |
| 6,142,811 A | 11/2000 | Lin |
| 6,146,811 A | 11/2000 | Kim et al. |
| 6,169,139 B1 | 1/2001 | van Cleeff |
| 6,204,343 B1 | 3/2001 | Barucha et al. |
| 6,276,273 B1 | 8/2001 | Aurenty et al. |
| 6,309,580 B1 | 10/2001 | Chou |
| 6,334,960 B1 | 1/2002 | Willson et al. |
| 6,372,838 B1 | 4/2002 | Rao et al. |
| 6,375,870 B1 | 4/2002 | Visovsky et al. |
| 6,447,919 B1 | 9/2002 | Brown |
| 6,468,642 B1 | 10/2002 | Bray et al. |
| 6,503,914 B1 | 1/2003 | Benish et al. |
| 6,544,594 B2 | 4/2003 | Linford et al. |
| 6,565,776 B1 | 5/2003 | Li et al. |
| 6,649,272 B2 | 11/2003 | Moore et al. |
| 6,664,306 B2 | 12/2003 | Gaddam et al. |
| 6,664,354 B2 | 12/2003 | Savu et al. |
| 6,696,220 B2 | 2/2004 | Bailey et al. |

(Continued)

FOREIGN PATENT DOCUMENTS

| | | |
|---|---|---|
| EP | 0465039 | 1/1992 |
| EP | 0540203 | 5/1993 |

(Continued)

OTHER PUBLICATIONS

Johnson et al., Advances in Step and Flash Imprint Lithography, SPIE Microlithography Conference Feb. 23, 2003.
Bender et al., Fabrication of Nanostructures using a UV-based Imprint Technique, Microelectronic Engineering 53, pp. 233-236 Jan. 1, 2000.
Bender et al., Multiple Imprinting in UV-based Nanoimprint Lithography: Related Material Issues, Microelectronic Engineering 61-62. pp. 407-413 Jan. 1, 2002.
Chou et al., Ultrafast and Direct Imprint of Nanostructures in Silicon, Nature, col. 417, (Jun. 2002), pp. 835-837 Jun. 1, 2002.
Chou et al., Nanoimprint Lithography, Journal of Vacuum Science Technology B 14(16), pp. 4129-4133 Nov. 1, 1996.
Bailey et al., Step and Flash Imprint Lithography: Template Surface Treatment and Defect Analysis, Journal of Vacuum Science, B 18(6), pp. 3572-3577 Nov. 1, 2000.
Novec Fluorasurfactant FC-4432, http://multimedia.mmm.com/mediawebserver/dyn?333333SQa783cMj3wMj333wyXuFiiiiH— Aug. 4, 2005.

(Continued)

Primary Examiner — Sanza McClendon
(74) Attorney, Agent, or Firm — Heather L. Flanagan; Fish & Richardson P.C.

(57) ABSTRACT

Release agents with increased affinity toward nano-imprint lithography template surfaces interact strongly with the template during separation of the template from the solidified resist in a nano-imprint lithography process. The strong interaction between the surfactant and the template surface reduces the amount of surfactant pulled off the template surface during separation of a patterned layer from the template in an imprint lithography cycle. Maintaining more surfactant associated with the surface of the template after the separation of the patterned layer from the template may reduce the amount of surfactant needed in a liquid resist to achieve suitable release of the solidified resist from the template during an imprint lithography process. Strong association of the release agent with the surface of the template facilitates the formation of ultra-thin residual layers and dense fine features in nano-imprint lithography.

23 Claims, 8 Drawing Sheets

(56) References Cited

U.S. PATENT DOCUMENTS

| | | |
|---|---|---|
| 6,721,529 B2 | 4/2004 | Chen et al. |
| 6,737,489 B2 | 5/2004 | Linert et al. |
| 6,774,183 B1 | 8/2004 | Palumbo et al. |
| 6,790,905 B2 | 9/2004 | Fitzgerald et al. |
| 6,802,870 B2 | 10/2004 | Chang et al. |
| 6,830,819 B2 | 12/2004 | Kaplan et al. |
| 6,873,087 B1 | 3/2005 | Choi et al. |
| 6,932,934 B2 | 8/2005 | Choi et al. |
| 6,936,194 B2 | 8/2005 | Watts |
| 6,957,608 B1 | 10/2005 | Hubert |
| 7,037,574 B2 | 5/2006 | Paranjpe |
| 7,077,992 B2 | 7/2006 | Sreenvisan |
| 7,157,036 B2 | 1/2007 | Choi et al. |
| 7,179,396 B2 | 2/2007 | Sreenivasan |
| 7,307,118 B2 | 12/2007 | Xu et al. |
| 7,837,921 B2 | 11/2010 | Xu et al. |
| 2001/0055727 A1 | 12/2001 | Kubota et al. |
| 2002/0072009 A1 | 6/2002 | Kim et al. |
| 2002/0084553 A1 | 7/2002 | Nun et al. |
| 2002/0115002 A1 | 8/2002 | Bailey et al. |
| 2002/0126189 A1 | 9/2002 | Gloster |
| 2002/0135099 A1 | 9/2002 | Robinson et al. |
| 2002/0146642 A1 | 10/2002 | Kim et al. |
| 2003/0166814 A1 | 9/2003 | Sparrowe et al. |
| 2004/0046288 A1 | 3/2004 | Chou |
| 2004/0065252 A1 | 4/2004 | Sreenivasan et al. |
| 2004/0065976 A1 | 4/2004 | Sreenivasan et al. |
| 2004/0116548 A1 | 6/2004 | Willson et al. |
| 2004/0137734 A1 | 7/2004 | Chou et al. |
| 2004/0168613 A1 | 9/2004 | Nguyen et al. |
| 2004/0211754 A1 | 10/2004 | Sreenivasan |
| 2005/0160934 A1 | 7/2005 | Xu et al. |
| 2005/0187339 A1 | 8/2005 | Xu et al. |
| 2005/0192421 A1 | 9/2005 | Xu et al. |
| 2005/0236739 A1 | 10/2005 | Willson et al. |
| 2006/0035029 A1 | 2/2006 | Xu et al. |
| 2006/0036051 A1 | 2/2006 | Xu et al. |
| 2006/0062867 A1 | 3/2006 | Choi et al. |
| 2006/0062922 A1 | 3/2006 | Xu et al. |
| 2006/0076717 A1 | 4/2006 | Sreenivasan et al. |
| 2006/0077374 A1 | 4/2006 | Sreenivasan et al. |
| 2006/0081557 A1 | 4/2006 | Xu et al. |
| 2006/0108710 A1 | 5/2006 | Xu et al. |
| 2006/0145398 A1 | 7/2006 | Bailey et al. |
| 2006/0279024 A1 | 12/2006 | Choi et al. |
| 2007/0017631 A1 | 1/2007 | Xu |
| 2007/0021520 A1 | 1/2007 | Xu |
| 2007/0141271 A1 | 6/2007 | Xu et al. |
| 2007/0272825 A1 | 11/2007 | Xu et al. |
| 2008/0000373 A1 | 1/2008 | Petrucci-Samija |
| 2008/0110557 A1 | 5/2008 | Xu |
| 2009/0136654 A1 | 5/2009 | Xu et al. |
| 2009/0149616 A1* | 6/2009 | Audenaert et al. ............ 526/247 |
| 2009/0272875 A1 | 11/2009 | Xu et al. |
| 2010/0109195 A1 | 5/2010 | Xu et al. |
| 2011/0031651 A1 | 2/2011 | Xu et al. |
| 2011/0215503 A1 | 9/2011 | Xu |

FOREIGN PATENT DOCUMENTS

| | | |
|---|---|---|
| EP | 1342736 A2 | 9/2003 |
| EP | 1491356 A2 | 12/2004 |
| EP | 05722972 | 11/2006 |
| WO | WO 97/31071 | 8/1997 |
| WO | WO 00/46035 | 8/2000 |
| WO | WO 00/54107 | 9/2000 |
| WO | WO 02/069040 | 9/2002 |
| WO | WO 03/073164 A2 | 9/2003 |
| WO | WO 2004/061526 | 7/2004 |
| WO | WO/2005/000552 | 6/2005 |
| WO | WO 2005/072120 | 8/2005 |
| WO | WO/2005/082992 | 9/2005 |
| WO | WO 2006/057843 | 6/2006 |
| WO | WO/2007/133235 | 11/2007 |

OTHER PUBLICATIONS

Xu et al., Development of Imprint Materials for the Step and Flash Imprint Lithography Process, SPIE Microlithography Conference Feb. 1, 2004.

Colburn, Dissertation for the Degree of Doctor of Philosophy, Step and Flash Imprint Lithography: A Low-Pressure, Room-Temperature Nanoimprint Lithography Aug. 1, 2001.

DuPont Zonyl Fluorochemical Intermediates, www.dupont.com/zonyl/pdf/intermediates.pdf, pp. 1-16 Jun. 21, 2003.

DuPont Zonyl UR, www.dupont.com/zonyl/pdf/UR.pdf; pp. 1-2 Jun. 21, 2003.

DuPont Zonyl FSN, www.dupont.com/zonyl/odf/FSN.pdf; pp. 1-2 Aug. 24, 2003.

Masurf FS-230, www.masonsurfactants.com/Products/Masurf_FS_230.htm; pp. 1-2 Apr. 5, 2004.

FC-4432 Product Brochure, 3M Fluorad Fluorosurfactant Mar. 1, 2002.

Jung et al., Orientation-Controlled Self-Assembled Nanolithography Using a Polystyrene-Polydimethylsiloxane Block Copolymer, Nano Letters, vol. 7, No. 7, pp. 2046-2050 (2007) Apr. 19, 2007.

Komuro et al., Improvement of Imprinted Pattern Uniformity Using Sapphire Mold, Jpn J.Appl. Phys. vol. 41 pp. 4182-4185 Jun. 10, 2002.

Taniguchi et al., Measurement of Adhesive Force Between Mold and Photocurable Resin in Imprint Lithography, Japan. J. Appl. Phys., 41 (2002) pp. 4194-4197 Jan. 1, 2002.

Fukuhara et al., UV Nanoimprint Lithography and Its Application for Nanodevices, Journal of Photopolymer Science and Technology 20:4 (2007) pp. 549-554 May 10, 2007.

Guo, Nanoimprint Lithography: Methods and Material Requirements, Advanced Materials 19 (2007) pp. 495-513 Jan. 1, 2007.

Kim et al., Fabrication of trilayer resist using photocuring-imprint lithography, Journal of Vacuum Science and Technology B 21:6 (2003) pp. 3144-3148 Dec. 10, 2003.

Voisin et al., Characterisation of ultraviolet nanoimprint dedicated resists, Microelectronic Engineering 84 (2007) pp. 967-972 Feb. 1, 2007.

Scheerlinck et al., Nano Imprint Lithography for Photonic Structure Patterning, Proceedings Symposium IEEE/LEOS Beneliux Chapter Mons. pp. 63-66 Jan. 1, 2005.

Lin et al., Role of surfactants in adhesion reduction for step and flash imprint lithography, J. Micro/Nanolith., MEMS MOEMS 7(3) Jul.-Sep. 2008 Jul. 1, 2008.

Zhaohui et al., Surface activity of perfluorodecanoyl end-capped poly(ethylene oxide) and associated adsorption behavior to the air-water interface, Polymer, Elsevier Science Publishers B.V., GB, vol. 39 No. 19 p. 4659, 4660 Sep. 1, 1998.

Bongiovanni et al., High resolution XPS investigation of photocured fils containing perfluoropolyether acrylates, Polymer, Elsevier Science Publishers B.V., GB, vol. 41 No. 2 pp. 409-414 Jan. 1, 2000.

Masurf FS-230, www.masonsurfactants.com/Products/Masurf_FS_230.htm, pp. 1-2, Apr. 5, 2004.

International Search Report for Application No. PCT/US2004/18857, dated Apr. 26, 2005, 2 pages.

International Search Report for Application No. PCT/US2005/001054, dated Aug. 29, 2005, 1 page.

International Search Report for Application No. PCT/US05/04415, dated Jun. 15, 2005, 1 page.

International Search Report for Application No. PCT/US2009/005990, dated Sep. 15, 2010, 11 pages.

European Search Report for Application No. EP10181754, dated Oct. 26, 2010, 6 pages.

European Search Report for Application No. EP05820878, dated Oct. 28, 2010, 8 pages.

International Search Report for Application No. PCT/US2008/013827, dated Apr. 7, 2009, 1 page.

Written Opinion for Application No. PCT/US2008/013827, dated Apr. 7, 2009, 4 pages.

International Search Report and Written Opinion for Application No. PCT/US2005/41156, dated May 10, 2006, 7 pages.

* cited by examiner

Structures 5-9

Structure 10

Structure 11

Structure 12

RELEASE AGENT PARTITION CONTROL IN IMPRINT LITHOGRAPHY

CROSS-REFERENCE TO RELATED APPLICATIONS

This application is a continuation of U.S. application Ser. No. 12/612,527, filed Nov. 4, 2009, which claims the benefit under 35 U.S.C. §119(e)(1) of U.S. Provisional Application Ser. No. 61/111,509, filed Nov. 5, 2008, both of which are incorporated by reference herein in their entirety.

TECHNICAL FIELD

The present invention relates to release agent partition control in nano-imprint lithography.

BACKGROUND

Nano-fabrication includes the fabrication of very small structures that have features on the order of 100 nanometers or smaller. One application in which nano-fabrication has had a sizeable impact is in the processing of integrated circuits. The semiconductor processing industry continues to strive for larger production yields while increasing the circuits per unit area formed on a substrate, therefore nano-fabrication becomes increasingly important. Nano-fabrication provides greater process control while allowing continued reduction of the minimum feature dimensions of the structures formed. Other areas of development in which nano-fabrication has been employed include biotechnology, optical technology, mechanical systems, and the like.

An exemplary nano-fabrication technique in use today is commonly referred to as imprint lithography. Exemplary imprint lithography processes are described in detail in numerous publications, such as U.S. Patent Application Publication No. 2004/0065976, U.S. Patent Application Publication No. 2004/0065252, and U.S. Pat. No. 6,936,194, all of which are hereby incorporated by reference herein.

An imprint lithography technique disclosed in each of the aforementioned U.S. patent application publications and patent includes formation of a relief pattern in a formable (polymerizable) layer and transferring a pattern corresponding to the relief pattern into an underlying substrate. The substrate may be coupled to a motion stage to obtain a desired positioning to facilitate the patterning process. The patterning process uses a template spaced apart from the substrate and the formable liquid applied between the template and the substrate. The formable liquid is solidified to form a rigid layer that has a pattern conforming to a shape of the surface of the template that contacts the formable liquid. After solidification, the template is separated from the rigid layer such that the template and the substrate are spaced apart. The substrate and the solidified layer are then subjected to additional processes to transfer a relief image into the substrate that corresponds to the pattern in the solidified layer.

SUMMARY

Release agents with increased affinity toward nano-imprint lithography template surfaces interact strongly with the template during separation of the template from the solidified resist in a nano-imprint lithography process. The strong interaction between the surfactant and the template surface reduces the amount of surfactant pulled off the template surface during separation of a patterned layer from the template in an imprint lithography cycle. Maintaining more surfactant associated with the surface of the template after the separation of the patterned layer from the template may reduce the amount of surfactant needed in a liquid resist to achieve suitable release of the solidified resist from the template during an imprint lithography process. Strong association of the release agent with the surface of the template facilitates the formation of ultra-thin residual layers and dense fine features in nano-imprint lithography.

In one aspect, an imprint lithography release agent includes a non-polar fluorinated portion and a polar poly(oxyalkylene) portion bonded to the non-polar fluorinated portion. The polar poly(oxyalkylene) portion is formed from a multiplicity of oxyalkylene units including at least one ethylene oxide unit. The release agent is capable of forming multiple polar interactions with a surface of an imprint lithography template.

In another aspect, an imprint lithography liquid resist includes a monomer, a cross-linking agent, a photoinitiator, a catalyst, and an imprint lithography release agent.

In another aspect, an imprint lithography mold assembly includes an imprint lithography substrate, a polymerizable material disposed on the substrate, and an imprint lithography template having a surface. The surface of the imprint lithography template is in contact with the polymerizable material. The polymerizable material includes an imprint lithography release agent.

Another aspect includes disposing a polymerizable composition on an imprint lithography substrate, contacting the polymerizable composition with an imprint lithography template, solidifying the polymerizable composition to form a patterned layer adhered to the imprint lithography substrate, and separating the imprint lithography template from the solidified patterned layer. The polymerizable composition includes an imprint lithography release agent. Contacting the polymerizable composition with the imprint lithography template includes forming multiple polar interactions between the release agent and the surface of the imprint lithography template.

In another aspect, forming an imprint lithography template includes cleaning a template to form hydroxyl groups on the surface of the template, introducing a metal-containing compound to react with the surface hydroxyl groups, introducing water vapor to form metal-OH on the surface of the template, and annealing the metal-OH to form a layer of metal oxide on the surface of the template. The surface of the template is capable of forming ionic and polar interactions with an imprint lithography release agent. In some implementations, the metal-containing compound is $Al(CH_3)_3$.

Implementations may include one or more of the following features. The release agent may be non-ionic. The release agent may have no silane functionality. A molecular weight of the release agent may be at least about 1000 amu or at least about 2000 amu. The release agent may form multiple polar interactions with the surface of an imprint lithography template. For example, the release agent may form hydrogen bonding interactions with hydroxyl groups or silanol groups at the surface of the imprint lithography template. The imprint lithography template may include fused silica, and may be processed to increase a number of hydroxyl groups at the surface.

The polar poly(oxyalkylene) portion of the release agent can be formed from a multiplicity of oxyalkylene units including at least three ethylene oxide units, at least five ethylene oxide units, or at least ten ethylene oxide units. The polar poly(oxyalkylene) portion of the release agent can be formed from a multiplicity of oxyalkylene units including at least one propylene oxide unit, at least three propylene oxide units, or at least five propylene oxide units. The fluorinated portion of the imprint lithography release agent can include a perfluorinated polyether portion. The release agent may be a liquid at room temperature.

The release agent may include two or more hydroxyl groups. The hydroxyl groups may be terminal hydroxyl groups. In some cases, the release agent includes one or more carboxyl groups. One or more of the carboxyl groups may be terminal carboxyl groups. Polar interactions between the imprint lithography release agent and the surface of the template can include cyclic hydrogen bonding interactions with hydroxyl groups or carboxyl groups.

In some cases, the release agent includes an atom capable of forming a stronger polar interaction with the template than a hydrogen bonding interaction. For example, the release agent can include one or more nitrogen atoms. One or more of the nitrogen atoms may be part of a heterocycle, such as a pyridazinyl group.

In some cases, the imprint lithography release agent does not bond covalently to the template. In certain cases, the release agent includes an atom capable of forming a covalent bond with the surface of the imprint lithography template. The covalent bond may have a strength less than the strength of a silicon-oxygen bond at the surface of the template. For example, the release agent may include a boron atom capable of forming a weak covalent bond or quasi-covalent bond with the surface of the template.

In some implementations, the imprint lithography release agent has the chemical structure:

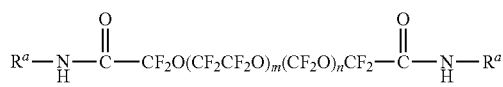

Each $R^a$ is independently $H_3C[OCH_2CH_2]_x[OCH_2CHCH_3]_y$—, and m and n and x and y are integers.

When the release agent is included in a liquid resist, contacting the liquid resist with a surface of the template may form a lamella layer including the release agent at the surface of the imprint lithography template. In some cases, the liquid resist includes a compound including a perfluorinated polyether portion and one or more acrylate groups. When the imprint lithography template is separated from the solidified patterned layer in an imprint lithography process, less than about 50%, less than about 40%, less than about 30%, or less than about 20% of the polar interactions between the release agent and the surface of the imprint lithography template may be broken. That is, at least about 50%, at least about 60%, at least about 70%, or at least about 80% of the release agent associated with the template during formation of the patterned layer may remain associated with the template after the template is separated from the solidified resist in an imprint lithography cycle.

Aspects and implementations described herein may be combined in ways other than described above. Other aspects, features, and advantages will be apparent from the following detailed description, the drawings, and the claims.

DETAILED DESCRIPTION

Figure 1:
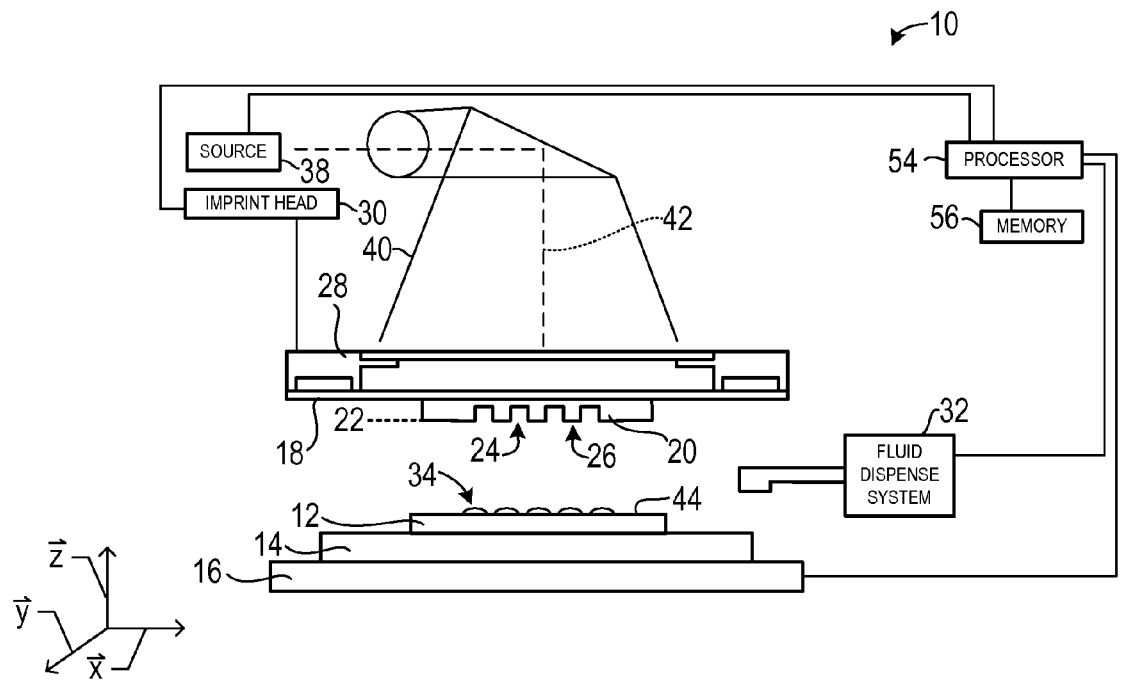
FIG. 1 illustrates a simplified side view of a lithographic system.

Referring to FIG. 1, illustrated therein is a lithographic system 10 used to form a relief pattern on substrate 12. Substrate 12 may be coupled to substrate chuck 14. As illustrated, substrate chuck 14 is a vacuum chuck. Substrate chuck 14, however, may be any chuck including, but not limited to, vacuum, pin-type, groove-type, electromagnetic, and/or the like. Exemplary chucks are described in U.S. Pat. No. 6,873,087, which is hereby incorporated by reference herein.

Substrate 12 and substrate chuck 14 may be further supported by stage 16. Stage 16 may provide motion about the x-, y-, and z-axes. Stage 16, substrate 12, and substrate chuck 14 may also be positioned on a base (not shown).

Spaced-apart from substrate 12 is a template 18. Template 18 generally includes a mesa 20 extending therefrom towards substrate 12, mesa 20 having a patterning surface 22 thereon. Further, mesa 20 may be referred to as mold 20. Template 18 and/or mold 20 may be formed from such materials including, but not limited to, fused-silica, quartz, silicon, organic polymers, siloxane polymers, borosilicate glass, fluorocarbon polymers, metal, hardened sapphire, and/or the like. As illustrated, patterning surface 22 comprises features defined by a plurality of spaced-apart recesses 24 and/or protrusions 26, though embodiments of the present invention are not limited to such configurations. Patterning surface 22 may define any original pattern that forms the basis of a pattern to be formed on substrate 12.

Template 18 may be coupled to chuck 28. Chuck 28 may be configured as, but not limited to, vacuum, pin-type, groove-type, electromagnetic, and/or other similar chuck types. Exemplary chucks are further described in U.S. Pat. No. 6,873,087, which is hereby incorporated by reference herein. Further, chuck 28 may be coupled to imprint head 30 such that chuck 28 and/or imprint head 30 may be configured to facilitate movement of template 18.

System 10 may further comprise a fluid dispense system 32. Fluid dispense system 32 may be used to deposit polymerizable material 34 on substrate 12. Polymerizable material 34 may be positioned upon substrate 12 using techniques such as drop dispense, spin-coating, dip coating, chemical vapor deposition (CVD), physical vapor deposition (PVD), thin film deposition, thick film deposition, and/or the like. Polymerizable material 34 may be disposed upon substrate 12 before and/or after a desired volume is defined between mold 20 and substrate 12 depending on design considerations. Polymerizable material 34 may comprise a monomer as described in U.S. Pat. No. 7,157,036 and U.S. Patent Application Publication No. 2005/0187339, all of which are hereby incorporated by reference herein.

Figure 2:
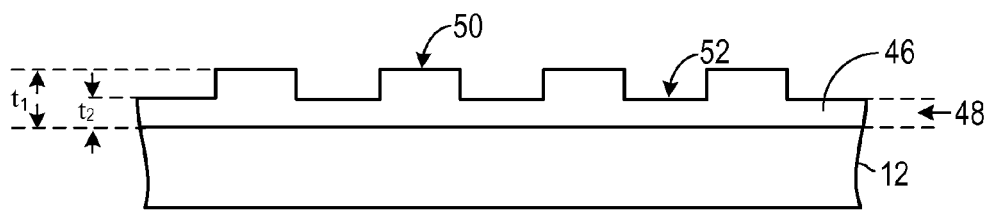
FIG. 2 illustrates a simplified side view of the substrate shown in FIG. 1 having a patterned layer positioned thereon.

Referring to FIGS. 1 and 2, system 10 may further comprise an energy source 38 coupled to direct energy 40 along path 42. Imprint head 30 and stage 16 may be configured to position template 18 and substrate 12 in superimposition with path 42. System 10 may be regulated by a processor 54 in communication with stage 16, imprint head 30, fluid dispense system 32, and/or source 38, and may operate on a computer readable program stored in memory 56.

Either imprint head 30, stage 16, or both vary a distance between mold 20 and substrate 12 to define a desired volume therebetween that is filled by polymerizable material 34. For example, imprint head 30 may apply a force to template 18 such that mold 20 contacts polymerizable material 34. After the desired volume is filled with polymerizable material 34, source 38 produces energy 40, e.g., broadband ultraviolet radiation, causing polymerizable material 34 to solidify and/or cross-link conforming to shape of a surface 44 of substrate 12 and patterning surface 22, defining a patterned layer 46 on substrate 12. Patterned layer 46 may comprise a residual layer 48 and a plurality of features shown as protrusions 50 and recessions 52, with protrusions 50 having a thickness $t_1$ and residual layer 48 having a thickness $t_2$.

The above-described system and process may be further implemented in imprint lithography processes and systems referred to in U.S. Pat. No. 6,932,934, U.S. Patent Application Publication No. 2004/0124566, U.S. Patent Application Publication No. 2004/0188381, and U.S. Patent Application Publication No. 2004/0211754, each of which is hereby incorporated by reference herein.

After patterned layer 46 is formed on substrate 12, template 18 or mold 20 is separated from the patterned layer. Separation of the mold or template from the patterned layer may be facilitated with an a priori release layer bonded to the template surface or a coating of surfactant on the template surface. In an a priori release method, a release layer is solidified and chemically bonded (i.e., covalently bonded) to the template surface. Thus, the surface stoichiometry of the template is altered through covalent bonding. One such a priori release layer includes a self-assembled monolayer formed from tridecafluoro-1,1,2,2-tetrahydrooctyltrichlorosilane (FOTS). In a surfactant-based or release agent method, surfactant is included in the polymerizable material. In this method, the surfactant does not undergo covalent bonding with the template surface, and the template surface stoichiometry is substantially unaltered.

In some cases, fluorinated surfactants in a polymerizable material or liquid resist may be used to facilitate separation of the template 18 from the patterned layer 46. When the template 18 is contacted with the polymerizable material 34, surfactant from the polymerizable material may orient to cover all or substantially all of the template surface. For example, when a template contacts polymerizable material that includes a fluorinated surfactant, the hydrophilic portion of some of the surfactant molecules may orient toward the template, and form hydrogen bonding interactions with the surface of the template, such that the hydrophobic, or fluorinated portion of these surfactant molecules extends away from the template surface and toward the polymerizable material on the substrate.

Other surfactant molecules at the surface of the polymerizable material may orient with the hydrophilic portion toward the bulk of the polymerizable material (i.e., toward the substrate) and with the hydrophobic portion extending away from the bulk (i.e., toward the template, or away from the substrate). When the template surface contacts the polymerizable material, a lamella layer may form between the surface of the template and the polymerizable material. The lamella layer may include the hydrophobic or fluorinated ends of surfactant molecules hydrogen bonded to the template surface, as well as the hydrophobic or fluorinated ends of surfactant molecules with their hydrophilic ends in the polymerizable material. When the surfactant or lamella layer covers all or substantially all of the template surface, separation of the template 18 from the patterned layer 46 may occur readily, such that the patterned layer is substantially defect-free.

Hydrogen bonding may be thought of as a polar interaction or attractive force in which a hydrogen atom from one source (e.g., a surfactant or a hydroxyl group at the surface of a template) is attracted to unshared electrons from another source (e.g., a hydroxyl group at the surface of a template or a surfactant, respectively). For example, a hydrogen atom in a surfactant may be attracted to unshared electrons in a hydroxyl group at the surface of a template, or a hydrogen atom in a hydroxyl group at the surface of a template may be attracted to unshared electrons in a surfactant, such that the surfactant is held at the surface of the template in the absence of covalent bonding. A hydrogen bonding interaction may have a fraction of the strength of a covalent bond.

During separation of the template 18 from the patterned layer 46, solidified polymeric material or imprinting resist may pull surfactant that is hydrogen bonded to the template surface away from the template, reducing the amount of surfactant hydrogen bonded to the template surface. As feature aspect ratios increase (e.g., as the ratio of the height to the width of protrusions 50 increases) and thickness $t_2$ of residual layer 48 decreases, the overall surface to volume ratio of the imprint resist increases. Thus, the amount of surfactant needed to cover the increased amount of template surface also increases (e.g., proportionally to the increase in surface area). A higher surfactant content in the imprint resist may reduce the void dissipation speed during fluid spreading and feature filling, thus increasing the time needed to form each patterned surface, and slowing down the throughput of a step and repeat imprint lithography process.

Fluorinated surfactants used in the polymerizable material or imprint resists may include one or more poly(oxyalkylenes). In some cases, surfactant molecules are terminated with a single hydroxyl group. These surfactant molecules may interact with and cling onto the template surface through hydrogen bonding interactions between silanol groups on the template surface and poly(oxyalkylene) oxygen in the surfactant, as well as hydrogen bonding interactions between silanol groups on the template surface and hydroxyl terminated groups in the surfactant. During the template separation step, the solidified resist may overcome some of these hydrogen bonding interactions and pull surfactant molecules away from the template through, for example, physical entanglement, thereby reducing the surfactant coverage of the template.

Figure 3:
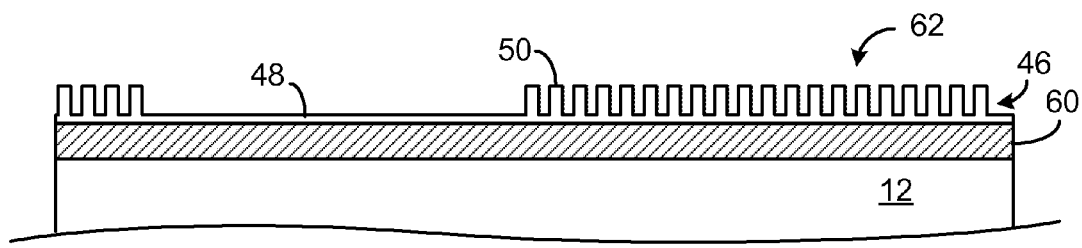
FIG. 3 illustrates a dense feature area formed by nanoimprint lithography.

There is an increasing need in imprinting lithography to fabricate dense fine features with an aspect ratio greater than 1:1 (e.g., about 2:1). At the same time, for the purpose of controlling critical dimensions (CDs) during reactive ion etching, the residual layer thickness may need to be less than about 50 nm, and in some cases less than about 15 nm. FIG. 3 illustrates a patterned layer 46 formed on imprint lithography substrate 12. Patterned layer 46 is adhered to transfer layer 60 on imprint lithography substrate 12. Patterned layer 46 includes thin residual layer 48 and protrusions 50. The protrusions 50 may be arranged in a dense feature area 62 formed by a block of fine features. Protrusions 50 extend from the residual layer 48 in dense feature area 62. The protrusions may be less than about 50 nm wide. In some cases, as depicted in FIG. 3, a ratio of the distance between the protrusions to the width of the protrusions is about 1:1. The aspect ratio of the protrusions (e.g., a ratio of the height to the width of the protrusions) may be at least about 2:1.

An imprinting cycle in a nano-imprinting process may be thought of as including two steps: a first step, in which liquid resist or polymerizable material is in contact with the template; and a second step, in which the template is separated from the solidified resist. The effectiveness of a template (e.g., the ability of a template to form substantially defect-free patterned layers) may be understood by depicting the amount of fluorine thought to be associated with the template surface for each step in the cycle versus the number of imprints made with the template.

Figure 4:
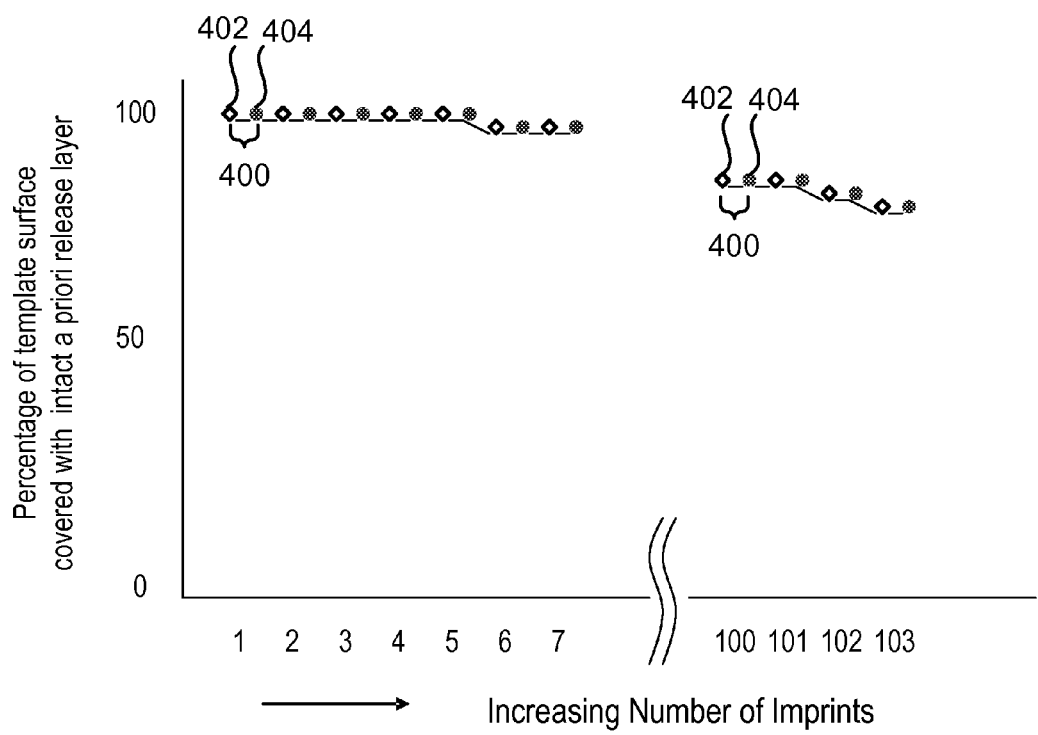
FIG. 4 illustrates fluorine content associated with a template surface with an a priori release layer versus number of imprints made with the template.

FIG. 4 illustrates the amount of fluorine associated with a hypothetical template surface, or the percentage of the template covered with intact (fluorine containing) a priori release layer as a function of number of imprints made in succession. Each imprinting cycle 400 includes first step 402, in which liquid resist or polymerizable material is in contact with the template, and second step 404, in which the template is separated from the solidified resist. For an a priori release layer, the percentage of the template surface covered with fluorine (or an intact a priori release layer) is the highest for a low number of imprints (i.e., when a new template is first used), as seen for imprinting cycles 1 through 5. The a priori release layer gradually degrades with successive imprinting steps, and the fluorine content on the template surface is reduced, depicted in FIG. 4 as beginning with imprinting cycle 6. For an a priori release layer including FOTS, for example, a decrease in release performance is observed (i.e., the patterned layers formed are not substantially defect free) after 50 to 100 imprints.

Once the bonded fluorinated coating is damaged, the release performance may not be recoverable. This may be understood by looking at the structure of chemicals, such as FOTS, used to form an a priori release layer, as well as the covalent bonds between the FOTS and the template surface. FOTS bonds to a template surface through a non-fluorinated portion of the molecule. When the non-fluorinated portion of the molecule is bonded to the surface of the template, the fluorinated portion of the FOTS extends from the surface of the template. Although the fluorinated portion may degrade (e.g., fragments of the molecule including fluorine may break off) with use over time (i.e., with an increasing number of imprints), the base portion of the molecule may remain covalently bonded to the template surface. Whereas patterned layers separate easily and substantially defect-free from fully fluorinated regions of the template surface, adhesion between the imprint resist and regions of the template surface where the base portions lose the fluorinated portions inhibits separation between the patterned layer and the template surface, increasing the force necessary to separate the template and the imprint resist, and resulting in patterned layers with defects. There is no self-repair mechanism known for the a priori release layer once fluorinated portions of the surface break off.

Figure 5:
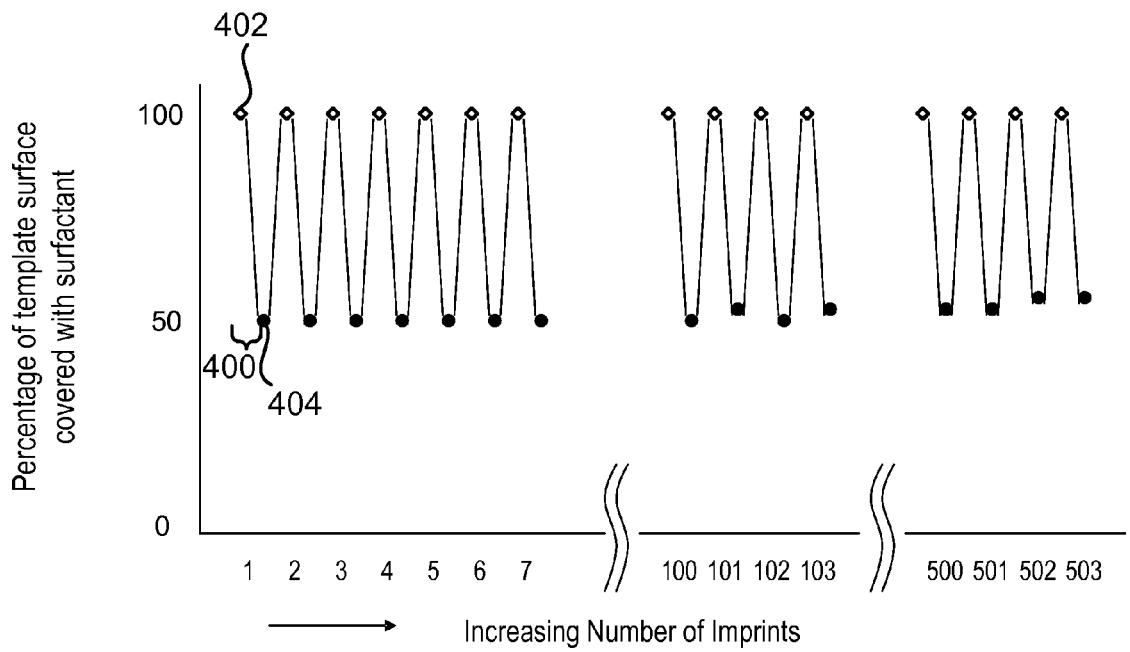
FIG. 5 illustrates fluorine content associated with a template surface versus number of imprints made with the template for a surfactant-based release method.

FIG. 5 illustrates a content of fluorine associated with a template surface without an a priori release layer for steps 402 and 404 of imprinting cycles 400 versus number of imprints for a surfactant method in which a fluorinated surfactant is included in the polymerizable material. No fluorine-containing species are covalently bonded to the surface of the template (i.e., there is no a priori release layer on the template). A solidified resist may pull some surfactant off the template surface during separation of the template from the patterned layer in step 404. During the next imprint, however, surfactant in the polymerizable material supplies additional fresh surfactant to replace the surfactant depleted template surface in step 402. In this approach, the surfactant is associated with the template surface via polar (e.g., hydrogen bonding) interactions.

In the surfactant-based method in which a polymerizable material used as an imprint resist includes a surfactant and there is no a priori release layer on the template, fluorinated surfactant at the template surface is restored during each imprinting cycle, such that long imprinting runs on the order of thousands to tens of thousands of imprints may be achieved without noticeable degradation of imprinting quality. That is, the patterned layers are still substantially defect-free even after a template has been used successively in thousands of imprinting cycles without any intervening treatment of the template. The fluorinated surfactant may be dynamically exchanged off the template by the physical entanglement with the solidified resist during template separation because the surfactant is not covalently bonded to template. It is believed that this removal process occurs without fragmentation and degradation of the surfactant molecules. Thus, for templates without an a priori release layer used with a suitable surfactant-containing polymerizable material in a surfactant method, regions of the template surface may not be characterized by the higher release force observed with a priori release layers as the a priori release layers degrade over time.

The surfactant in a polymerizable material used as an imprint resist is thought to form polar interactions with the template, such that the template is associated with the hydrophilic portion of the surfactant and the fluorinated portion of the surfactant is oriented away from the template. At the same time, some surfactant molecules from the liquid resist approach the liquid/gas interface before imprinting, such that the fluorinated portion of some surfactant molecules in the liquid resist point toward the air (gas)/liquid interface. When the template touches the liquid resist, the fluorinated portion of the surfactant associated with the template and the fluorinated portion of the surfactant in the liquid resist are thought to meet and form a lamella layer including the hydrophobic, fluorinated portions of the surfactant molecules sandwiched between the hydrophilic portions of the surfactant molecules. The lamella layer enhances the release performance of the template by facilitating separation of the solidified resist from the template at the lamella layer.

Some fluorinated surfactants used to facilitate separation of an imprint resist from a template surface are described in U.S. Pat. No. 7,307,118 to Xu et al., which is incorporated by reference herein. Fluorinated surfactants may have a hydrophilic portion and a fluorine-rich hydrophobic portion. The hydrophilic portion may include a poly(oxyalkylene) group. A non-ionic fluorinated surfactant with poly(oxyalkylene) groups can be represented as

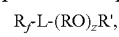

referred to herein as a Structure 1 surfactant. In Structure 1, $(RO)_z$ is a poly-(oxyalkylene) with oxyalkyl groups having two to four carbon atoms (e.g., R is —$CH_2CH_2$—, —$CH_2CH_2CH_2$—, —$CH(CH_3)CH_2$—, or —$CH(CH_3)CH(CH_3)$—); z is an integer; R' is a terminal group of H or $C_1$ to $C_4$ alkyl; and $R_f$ is a fluorine-containing portion which can include, but is not limited to, fluorinated alkyl groups, fluorinated ether groups, or a combination thereof. L is a carbon-containing linker group that links hydrophobic portion $R_f$ and hydrophilic portion $(RO_z)R'$ together.

Figure 6:
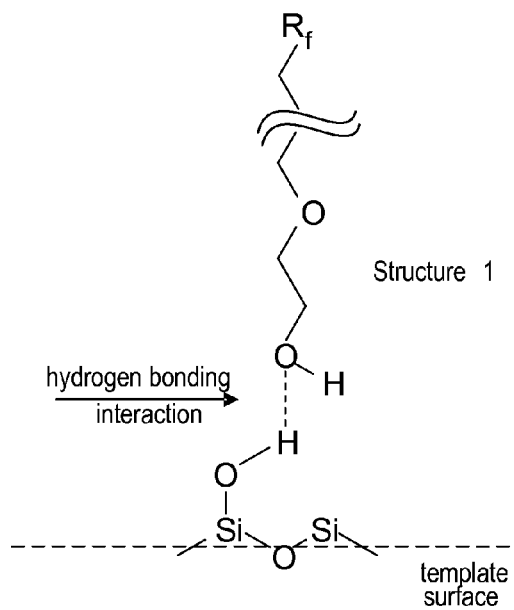
FIG. 6 illustrates surfactant-template hydrogen bonding interactions for a surfactant with a single terminal hydroxyl group.

Structure 1 will associate with a template via hydrogen bonding interactions between i) silanol groups on a template (Si—OH) and oxygen atoms in the poly(oxyalkylene); and between ii) silanol groups on the template and oxygen or hydrogen atoms in the terminal group (e.g., a terminal hydroxyl group). An example of a hydrogen bonding interaction between silanol at a surface of a template and a terminal hydroxyl group in a Structure 1 surfactant is illustrated in FIG. 6.

An example of a Structure 1 surfactant is MASURF® FS-2000, available from Mason Chemical Company (Arlington Heights, Ill.). FIG. 5 illustrates that a cured resist may pull a significant fraction (e.g., about 50%) of a Structure 1 surfactant from a template after each template separation 404 in an imprinting cycle 400. In the case of ultra-thin residual layer imprinting applications such as the one shown in FIG. 3, the residual layer thickness may be on the order of 10 nm. A surfactant-rich layer on a surface of a 10 nm-thick layer of polymerizable material used as a liquid resist may be about 1 nm thick. In this case, the surface to volume ratio of the imprint resist may be thought of as about 10% (1 nm/10 nm). If about 50% of the surfactant is removed from the surface of the template during separation of the template from the resist, this amount of surfactant may be replaced in the next imprint. To replace the surfactant that was removed, then, about half of the surface layer, or about 5% of the polymerizable composition for a residual layer with a thickness of 10 nm, may be needed to provide surfactant necessary to achieve desired release properties in the next imprint. Thus, surfactant loading in the liquid resist to achieve suitable release of the patterned layer from the template may be estimated to be at least 5%. High surfactant loading (e.g., at least 3%) may also be needed for a template with a high aspect ratio. High surfactant loading, however, may reduce the void dissipation speed during fluid spreading and feature filling, slowing down the throughput in a step and repeat imprint lithography process.

Figure 7:
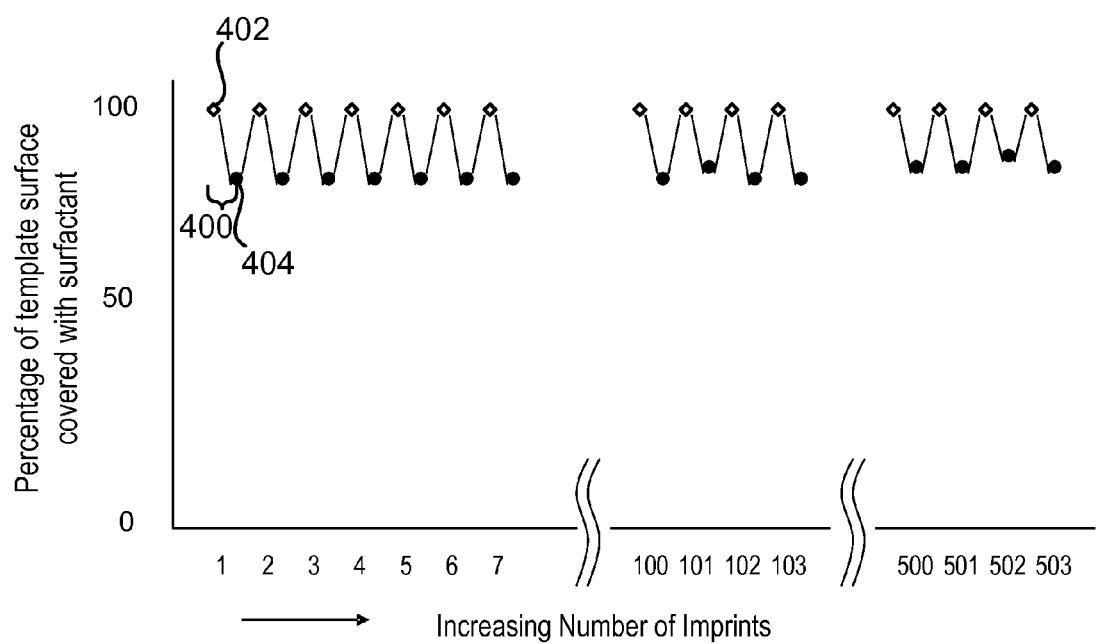
FIG. 7 illustrates fluorine content associated with a template surface versus number of imprints made with the template for a surfactant-based release method with stronger template-surfactant interactions than represented in FIG. 5.

FIG. 7 illustrates a qualitative plot of template surface fluorine content versus number of successive imprints for a surfactant-based imprint lithography process (no a priori release layer, surfactant in the liquid resist) that leaves more surfactant associated with the template surface through polar interactions than the example shown in FIG. 5. A surfactant that yields the results shown in FIG. 7 has more polar interactions, stronger polar interactions, or a combination of both with the template surface and is thus more difficult to remove from the template during an imprinting cycle 400. The surfactant distribution partition between template and solidified resist after separation is altered so that more surfactant molecules remain associated with the template surface than are pulled away from the template surface by the solidified resist. That is, surfactant molecules held to the template surface with stronger forces or interactions are less likely to be pulled off the template by physical entanglement with the solidified resist.

FIG. 7 illustrates that a cured resist may pull less (e.g., about 20%) of a surfactant off the template with each template separation when the surfactant is a more effective release agent and interacts more strongly with the template. Thus, for a residual layer with a thickness of 10 nm as discussed above, of the 10% of the liquid resist that makes up the surfactant-enriched surface layer, a smaller percentage (e.g., about 20%) may be needed to replace the surfactant removed from the template surface when the solidified resist is separated from the template in step 404. That is, the liquid resist may only need to supply enough surfactant to replace the surfactant molecules that are removed from the template in step 404. This amount may be estimated as 2% of the liquid resist composition for a surface to volume ratio of 10%. In this case, 2% surfactant loading by weight in the liquid resist may be sufficient to facilitate repeated, substantially defect-free release without adversely impacting fluid spreading and feature filling speed.

A surfactant capable of forming multiple hydrogen bonding interactions with a template surface is FLUOROLINK® E10, available from Solvay Solexis S.p.A (Italy). FLUOROLINK® E10 has the chemical formula:

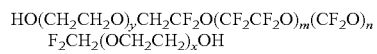

or $HO(EO)_yR'_f(EO)_xH$, in which EO refers to polyethylene oxide. Unlike Structure 1 surfactants, FLUOROLINK® E10 has two hydrophilic ends and one middle hydrophobic portion $R'_f$. $R'_f$ is a fluorinated ether segment with a molecular weight of about 1000 amu. An average value of x+y is about 3.5 to 4. FLUOROLINK® E10 may be added directly into a liquid resist. Even with two terminal hydroxyl groups, however, FLUOROLINK® E10 behaves similarly to Structure 1 surfactants, with similar surfactant partitioning between the template and the cured resist after the template is separated from the resist.

Increased hydrogen bonding strength between a surfactant and a template surface may be achieved with a surfactant having multiple sites capable of forming polar interactions with an imprint lithography template, a surfactant capable of forming stronger polar interactions with the template, or a combination of both. When a polymerizable material includes a surfactant with more or stronger polar interactions, a greater percentage of surfactant is retained on the template surface during separation of the template from the solidified resist. When a greater percentage of surfactant is retained on the template surface, less surfactant has to be replaced in each imprinting cycle, and thus the polymerizable composition can provide enhanced release performance with less surfactant.

Figure 8:
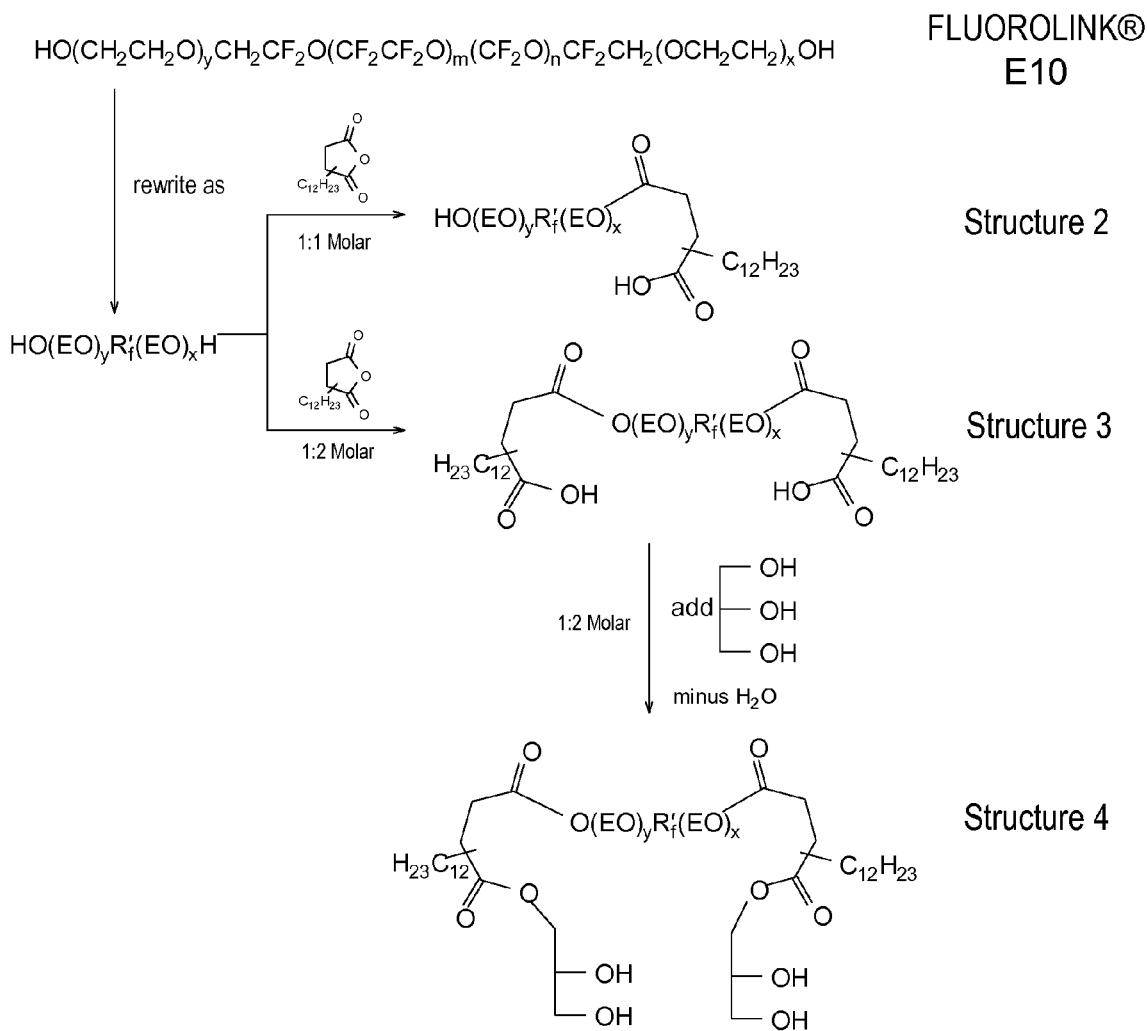
FIG. 8 shows a method for synthesizing surfactants with multiple sites able to form polar interactions with a surface of an imprint lithography template.

FIG. 8 illustrates synthesis of several surfactants able to interact more strongly with an imprint lithography template than Structure 1 surfactants or FLUOROLINK® E10.

Synthesis of Structure 2. FLUOROLINK® E10 (5 g, 4.2 mmol) and dodecenyl succinic anhydride (DDSA, 1.12 g, 4.2 mmol) were weighed into a flask. The flask was then connected to a bubbler to inhibit moisture interaction. The mixture was heated to 120-150° C. under stirring for about 3 hours. The reaction product, Structure 2, was cooled to room temperature and used without further purification.

Synthesis of Structure 3. FLUOROLINK® E10 (5 g, 4.2 mmol) and DDSA (2.24 g, 8.4 mmol) were weighed into a flask. The flask was then connected to a bubbler to inhibit moisture interaction. The mixture was heated to 120-150° C. under stirring for about 3 hours. The reaction product, Structure 3, was cooled to room temperature and used without further purification.

Synthesis of Structure 4. FLUOROLINK® E10 (5 g, 4.2 mmol) and DDSA (2.24 g, 8.4 mmol) were weighed into a flask. The flask was then connected to a bubbler to inhibit moisture interaction. The mixture was heated to 120-150° C.

under stirring for about 3 hours. The reaction mixture was cooled to room temperature, and glycerol (0.774 g, 8.4 mmol) was added to the reaction mixture. The mixture was then heated to 120-150° C. under stirring for about 3 hours. At this stage, the bubbler was removed in order to facilitate the escape of water. The resulting product, Structure 4, was cooled to room temperature and used without further purification.

Figure 9:
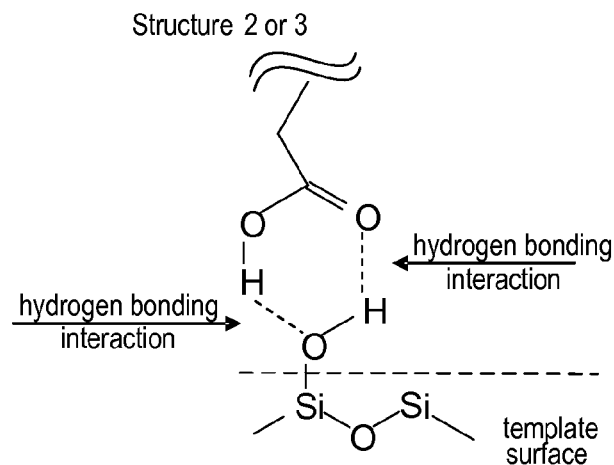
FIG. 9 illustrates surfactant-template hydrogen bonding interactions for a surfactant with a terminal carboxyl group.

The chemical structures and synthesis procedures above are exemplary, and may be modified to achieve suitable results. For example, instead of DDSA, succinic anhydride (SA) may be used to make other surfactants capable of interacting with a template similarly to Structures 2-4. In some cases, carboxylic groups may exist in both dimer and monomer forms. A single carboxylic group (as seen in Structures 2 and 3) may form strong hydrogen bonding interactions with a silanol group at a template surface as illustrated in FIG. 9, due at least in part to a cyclic structure formed by two or more hydrogen bonding interactions per surfactant molecule. Surfactant molecules held to the template surface with two or more hydrogen bonds, as illustrated in FIG. 9, may be held more strongly to the template than a surfactant molecule that shares one hydrogen bond with the template, as illustrated in FIG. 6.

In some embodiments, a carboxylic-terminated fluorinated ether (e.g., FLUOROLINK® C from Solvay Solexis) may be added directly into a resist (e.g., an acrylate-containing resist). In some cases, however, phase separation may occur, and the polymerizable fluid may become cloudy, indicative of the high fluorine content of FLUOROLINK® C. In contrast, however, Structures 2 and 3, and surfactants with similar structures, have good compatibility with acrylate-based resists. This is due at least in part to the —$CH_2CH_2O$— group and the DDSA group, making the overall structures more polar, and therefore more compatible with acrylate-based resists.

Figure 10:
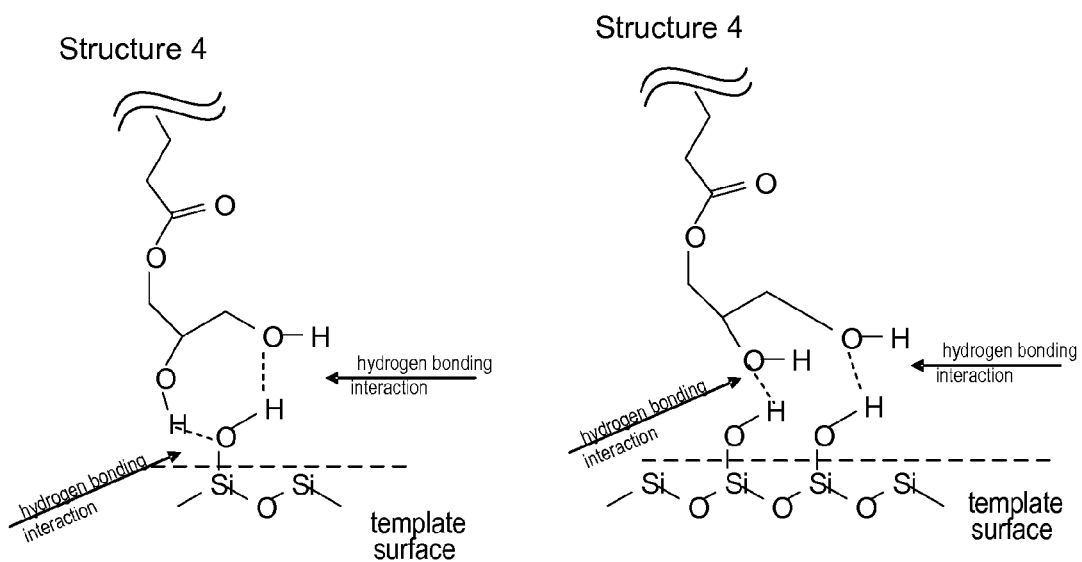
FIG. 10 illustrates surfactant-template hydrogen bonding interactions for a surfactant with more than one terminal hydroxyl group.

FIG. 10 illustrates hydrogen bonding interactions between a Structure 4 surfactant and silanol groups. The dual hydroxyl form of Structure 4 and similar surfactants may form strong hydrogen bonding interactions with a silanol group at a template surface, as illustrated in FIG. 10. The strong hydrogen bonding interactions may be due at least in part to the cyclic structure formed by two or more hydrogen bonding interactions and an increased number of hydrogen bonding interaction sites, including hydrogen bonding between the poly(oxyethylene) groups and the template. Surfactant molecules held to the template surface with two or more polar interactions, as illustrated in FIG. 10, may be associated with the template more strongly than a surfactant molecule that shares one hydrogen bond with the template, as illustrated in FIG. 6.

In addition to carboxylic groups and multiple hydroxyl groups in close vicinity, the strength of hydrogen bonding between a surfactant or release agent and a surface of a template may be increased by attaching other polar groups proximate the polar portion of a surfactant molecule such that the polar groups are able to form cyclic hydrogen bonding interaction structures or chelating cyclic hydrogen bonding interaction structures with silanol groups on a template surface. In an example, the attraction between a surfactant or release agent and a template may be increased by attaching longer polyethylene oxide (EO) chains and/or polypropylene oxide (PO) chains so that the surfactant or release agent can form multiple hydrogen bonding interactions with the template surface. The EO and PO chains can exist in the form of a block copolymer or a random copolymer.

An oxygen atom in an EO group may form a stronger hydrogen bonding interaction with a silanol group on the template surface than an oxygen atom in a PO group. For surfactants including a non-polar fluorinated portion and a polar poly(oxyakylene) portion bonded to the non-polar fluorinated portion, stronger interaction with a surface of a template is observed when at least one of the oxyalkylene units is ethylene oxide. Furthermore, within limits, surfactants with a higher molar ratio of EO to PO demonstrate stronger interaction with silanol groups on a template surface, and are more effective as imprint lithography release agents. Thus, these poly(oxyalkylene)-containing surfactants including (or formed from) at least one EO unit, at least 3 EO units, at least 5 E0 units, or at least 10 EO units provide desirable properties for use as release agents for imprint lithography.

The presence of PO in an imprint lithography release agent may increase the minimum molecular weight at which the polymer exists as a solid. Thus, the presence of PO may help achieve a higher molecular weight surfactant in a liquid state. The presence of PO may also help lower the contact angle of a liquid resist on the surface of a template. For at least these reasons, a poly(oxyalkylene)-containing surfactant for use as an imprint lithography release agent may include (or be formed from) at least one PO unit, at least 3 PO units, or at least 10 PO units.

In a comparison of interaction strength with an imprint lithography template, FLUOROLINK® E10, with the chemical structure HO(EO)$_y$R'$_f$(EO)$_x$H, in which an average value of x+y is about 3.5 to 4, demonstrates better performance as a release agent than perfluoropolyethers without poly(oxyalkylene) groups. FLUOROLINK® D10, for example, with a chemical structure HOCH$_2$CF$_2$O(CF$_2$CF$_2$O)$_m$(CF$_2$O)$_n$CF$_2$CH$_2$OH, does not interact as strongly with an imprint lithography template as FLUOROLINK® E10.

Increasing the EO and/or PO content of a surfactant or release agent may be achieved by adding EO and/or PO segments to, for example, surfactants such as FLUOROLINK® L10, FLUOROLINK® C10, and FOMBLIN® Z-DEAL available from Solvay Solexis. These surfactants have the general chemical formula shown below:

ROOC—CF$_2$O(CF$_2$CF$_2$O)$_m$(CF$_2$O)$_n$CF$_2$—COOR

For FLUOROLINK® L10, m/n=1.8-2.0, and R=C$_2$H$_5$. FLUOROLINK® L10 has two ester end groups and a middle hydrophobic (fluorinated) portion. The molecular weight of the fluorinated portion is about 1000 amu. For FLUOROLINK® C10, m/n=1.8-2.0, and R=H. FLUOROLINK® C10 has two carboxylic acid end groups and a middle hydrophobic (fluorinated) portion. The molecular weight of the fluorinated portion is about 1500 amu. For FOMBLIN® Z-DEAL, m/n=0.9-1.0, and R=CH$_3$. FOMBLIN® Z-DEAL has two ester end groups and a middle hydrophobic (fluorinated) portion. The molecular weight of the fluorinated portion is about 2000 amu.

EO and/or PO segments may be added to surfactants such as FLUOROLINK® L10, FLUOROLINK® C10, and FOMBLIN® Z-DEAL through a condensation reaction in which one or more EO- and/or PO-containing compounds, such as JEFFAMINE® M-2005, JEFFAMINE® M-2070, and JEFFAMINE® M-1000, are added to the surfactant via condensation reactions. JEFFAMINE® M-2005, JEFFAMINE® M-2070, and JEFFAMINE® M-1000, available from Huntsman Performance Products (The Woodlands, Tex.), include poly(oxyalkylene) segments as shown below.

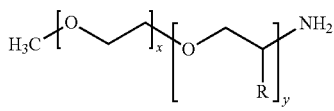

This formula can be expressed as $H_3C[OCH_2CH_2]_x[OCH_2CHR]_yNH_2$ or, when $R=CH_3$, as $H_3C[EO]_x[PO]_yNH_2$ or $R^aNH_2$. The EO and PO units may be present in a random or block copolymer type arrangement. For JEFFAMINE® M-1000, the mole ratio of PO/EO is about 3/19 and the molecular weight is about 1000 amu. For JEFFAMINE® M-2005, the mole ratio of PO/EO is about 29/16, and the molecular weight is about 2000 amu. For JEFFAMINE® M-2070, the mole ratio of PO/EO is about 10/31, and the molecular weight is about 2000 amu.

Figure 11:
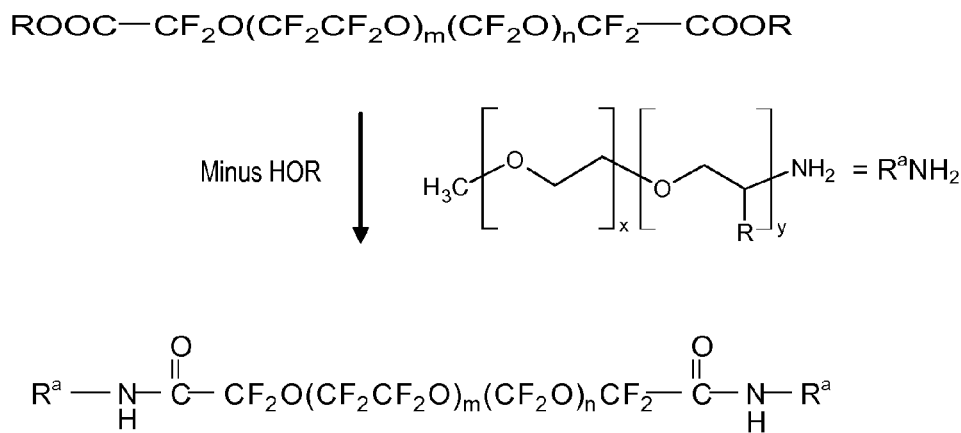
FIG. 11 illustrates a method for synthesizing imprint lithography release agents.

Surfactants that will interact more strongly with silanol groups on an imprint lithography template than any of Structures 1-4 can be synthesized by modifying the polar end groups of FLUOROLINK® L10, FLUOROLINK® C10, or FOMBLIN® Z-DEAL with JEFFAMINE® monoamines, as shown in FIG. 11. $R^a$ represents the $H_3C[EO]_x[PO]_y^-$ portion of the JEFFAMINE® M-2005, JEFFAMINE® M-2070, and JEFFAMINE® M-1000 molecules. The product formed in the reaction shown in FIG. 11 will vary based on the reactants or combination of reactants chosen. For example, the $R^a$ groups may be the same or different. That is, in some cases, two or more of JEFFAMINE® M-2005, JEFFAMINE® M-2070, and JEFFAMINE® M-1000 may be added, resulting in a surfactant in which a first $R^a$ originates from a different reactant than a second $R^a$. Examples of possible combinations are described by the synthesis of Structures 5-9.

Synthesis of Structure 5. FLUOROLINK® L10 (4 g, 3.5 mmol) and JEFFAMINE® M-1000 (6.9 g, 7.0 mmol) were weighed into a flask. The flask was then equipped with a nitrogen bubbler. The mixture was heated in a water bath to 30-60° C. under stirring. The reaction was followed by FT-IR until completion. The reaction product was cooled to room temperature and used without further purification.

Synthesis of Structure 6. FLUOROLINK® L10 (4 g, 3.5 mmol) and JEFFAMINE® M-2005 (14.2 g, 6.8 mmol) were weighed into a flask. The flask was then equipped with a nitrogen bubbler. The mixture was heated in a water bath to 30-60° C. under stirring. The reaction was followed by FT-IR until completion. The reaction product was cooled to room temperature and used without further purification.

Synthesis of Structure 7. FLUOROLINK® L10 (4 g, 3.5 mmol) and JEFFAMINE® M-2070 (14 g, 0.8 mmol) were weighed into a flask. The flask was then equipped with a nitrogen bubbler. The mixture was heated in a water bath to 30-60° C. under stirring. The reaction was followed by FT-IR until completion. The reaction product was cooled to room temperature and used without further purification.

Synthesis of Structure 8. FLUOROLINK® 010 (6 g, 3.8 mmol) and JEFFAMINE® M-2070 (15.7 g, 7.5 mmol) were weighed into a flask. The flask was then equipped with a nitrogen bubbler. The mixture was heated in a water bath to 30-60° C. under stirring. The reaction was followed by FT-IR until completion. The reaction product was cooled to room temperature and used without further purification. Reaction of FLUOROLINK® 010 with JEFFAMINE® M-2005 and JEFFAMINE® M-1000 can be achieved similarly.

Synthesis of Structure 9. FOMBLIN® Z-DEAL (3 g, 1.4 mmol) and JEFFAMINE® M-2070 (5.6 g, 2.7 mmol) were weighed into a flask. The flask was then equipped with a nitrogen bubbler. The mixture was heated in a water bath to 30-60° C. under stirring. The reaction was followed by FT-IR until completion. The reaction product was cooled to room temperature and used without further purification. Reaction of FOMBLIN® Z-DEAL with JEFFAMINE® M-2005 and JEFFAMINE® M-1000 can be achieved similarly.

The strength of a polar interaction between a nitrogen atom in a surfactant or release agent and a silanol group on the surface of a template may exceed the strength of a polar interaction between a hydrogen atom or an oxygen atom in a surfactant or release agent and a silanol group on the surface of the template. Thus, nitrogen-containing functional groups in a surfactant to be used as a release agent may interact more strongly with the template, and thus cling more strongly to the template during the separation of the template from the solidified resist. If the nitrogen-containing functional group is too basic, however, the performance of the resist may be compromised. One example of a suitable N-containing functional group is functionalized pyridazine, which can be grafted to a FLUOROLINK® L10 type of surfactant via a linking agent, such as diamine, as shown in FIG. 12.

Figure 12:
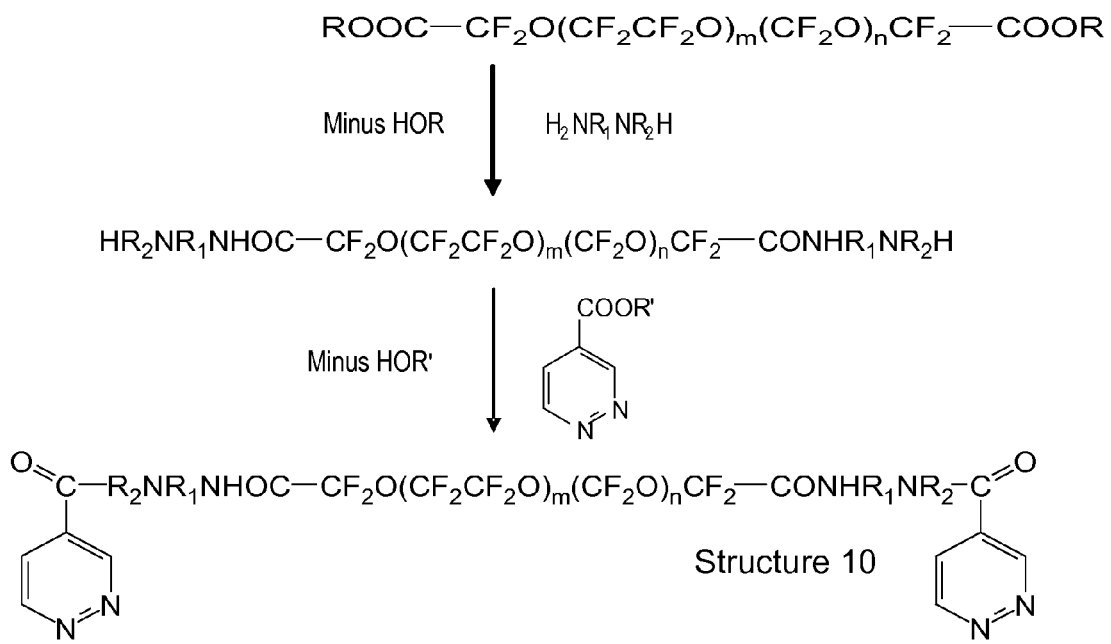
FIG. 12 illustrates a method for synthesizing imprint lithography release agents.

A FLUOROLINK® or FOMBLIN® surfactant undergoes a condensation reaction with a diamine, as shown in FIG. 12, in which $R_1$ and $R_2$ are carbon-containing. The resulting surfactant or release agent can then react with a functionalized pyridazine, in which R' is hydrogen or alkyl, to form a surfactant with Structure 10. Structure 10 aligns better on the surface of the template and is held more tightly to the template surface than other surfactants without a similar arrangement of hydrophilic, hydrophobic, and polar portions in the molecule.

Figure 13:
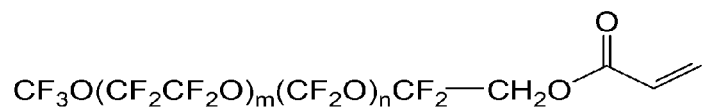
FIG. 13 illustrates chemical structures of some imprint lithography release agents.
Figure 13:
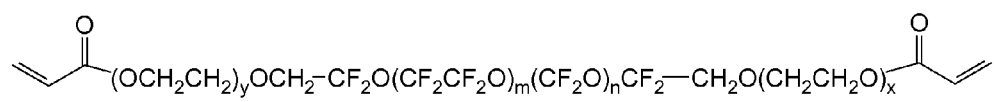

In some cases, fluorinated ether monoacrylates and fluorinated ether diacrylates can be added to a liquid resist to increase surface fluorine content without adversely affecting the release performance of Structures 5-9. Examples of a fluorinated ether monoacrylate and a fluorinated ether diacrylate are shown in FIG. 13 as Structures 11 and 12, respectively.

Compared to release agents with fluorinated alkyl hydrophobic portions, release agents with fluorinated ether hydrophobic portions of a similar molecular weight have a lower viscosity. Thus, while release agents with fluorinated alkyl hydrophobic portions may be solid at room temperature, release agents with fluorinated ether hydrophobic portions of a similar molecular weight may remain liquid at room temperature. For example, Structure 7 exists in the form of a liquid at room temperature. In contrast, a similar compound with a fluorinated alkyl portion, $—CF_3(CF_2)_n—$, with a molecular weight of 1000 amu and substantially the same length of EO and PO chains as Structure 7, is a solid at room temperature. Solid surfactants may not dissolve in the bulk resist used in an imprint lithography process. In addition, the backbone of a fluorinated ether portion is more flexible than the backbone of a fluorinated alkyl portion. Thus, the fluorinated ether portion may provide better lubricity for friction reduction during template separation.

Table 1 shows the physical state (solid or liquid) at room temperature of surfactants formed from poly(oxyalkylene) portions including EO only or a combination of EO and PO together with fluorinated alkyl or perfluorinated polyether portions.

TABLE 1

Physical state at room temperature of various surfactants.

|  | Fluorinated alkyl (1000-2000 amu) | Perfluorinated polyether (1000-2000 amu) |
|---|---|---|
| Poly(oxyalkylene) with EO and PO (liquid) | Solid | Liquid |
| Poly(oxyalkylene) with all or predominantly EO (solid) | Solid | Solid |

Table 1 shows that surfactants including a high molecular weight poly(oxyalkylene) with EO and PO (e.g., at least about 1000 amu, or at least about 2000 amu) are liquid at room temperature. When the surfactant is modified to include a fluorinated alkyl portion with a molecular weight of at least about 1000 amu, the resulting surfactant is a solid at room temperature. When the surfactant is modified to include a perfluorinated polyether (PFPE) with a molecular weight of at least about 1000 amu, the resulting surfactant is a liquid at room temperature. When the high molecular weight poly (oxyalkylene) includes only or predominantly EO, the poly (oxyalkylene) is a solid at room temperature. When the surfactant is modified to include a high molecular weight fluorinated alkyl group, the resulting surfactant is a solid at room temperature. Similarly, when the surfactant is modified to include a high molecular weight perfluorinated polyether (PFPE), the resulting surfactant is also found to be a solid at room temperature.

In some cases, a template/release agent anchoring mechanism may include weak covalent bonds that are stronger than polar interactions, such as hydrogen bonds, but weaker than Si—O—Si covalent bonds. In an a priori release approach, strong covalent Si—O—Si bonds are formed between the template surface and release agent. The strength of a hydrogen bonding interaction, however, may be a fraction of the strength of a Si—O bond. The strength of the interaction between a surfactant or release agent and a template may be increased by including an atom or functional group in the surfactant that interacts more strongly with a template surface than hydrogen, oxygen, or nitrogen, but less strongly than silicon. An atom or functional group capable of forming a weak or quasi-covalent bond with a template surface may improve the ability of the surfactant to perform as a release agent. In an example, a surfactant with a boron atom may form an interaction between the boron and the template surface. A fluorinated group may be bonded to the boron atom. A Si—O—B coupling, although considered to include covalent bonds, is weaker than a Si—O—Si coupling, which also includes covalent bonds. During separation of the template from the solidified resist, a bond in the Si—O—B coupling may break, such that a fluorinated group attached to the boron atom is removed from the template surface.

In some embodiments, a template surface may be modified to increase the strength of polar interactions between the template surface and a surfactant, or to provide an attractive force through charged (e.g., ionic) interaction. For example, a thin layer of metal oxide may be deposited onto a fused silica template. The metal oxide may include, for example, $AlO_x$. Deposition may be achieved through, for example, atomic layer deposition (ALD), as described in U.S. Pat. No. 7,037,574, which is incorporated by reference herein.

In an example, a fused silica template may be treated with a Piranha solution ($H_2SO_4:H_2O_2$ 3:1) to generate silanol (Si—OH) on the surface of the template. $Al(CH_3)_3$ vapor may be introduced to react with the surface Si—OH groups, followed by water vapor to generate Al—OH on the surface. One ALD cycle may deposit one molecular layer of $AlO_x$ on the surface. After a desired thickness of $AlO_x$ is achieved, a thermal or plasma process may be used to anneal the film. A high quality $AlO_x$ film, less than 5 nm thick, may be formed through this method.

Figure 14:
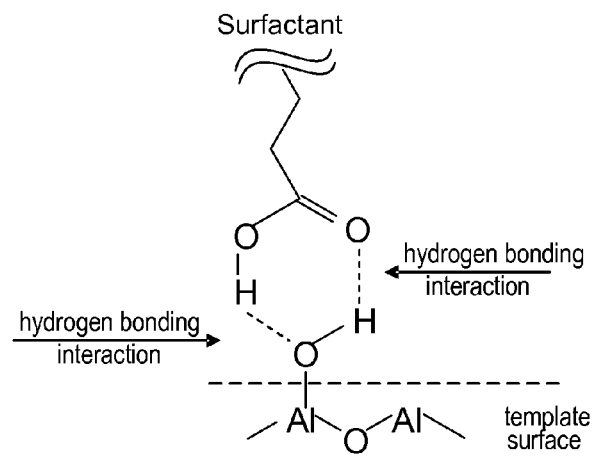
FIG. 14 illustrates surfactant-template hydrogen bonding interactions for a surfactant with a terminal carboxyl group and a template with an aluminum oxide layer on the surface.

The $AlO_x$ surface interacts with Structure 2 or 3 surfactants, such that the surfactants couple to the $AlO_x$ surface through both ionic interactions and hydrogen bonding interactions. The hydrogen bonding interaction is illustrated in FIG. 14. Comparing FIG. 14 and FIG. 11, the overall interactions between the template surface and surfactant Structures 2 and 3 may be stronger for an $AlO_x$ covered template surface than a fused silica template surface. The stronger interaction may be due to positive charges on the $AlO_x$ surface that interact ionically with carboxylic groups in the surfactant. The additional ionic interaction increases the attraction between Structure 2 and 3 surfactants and the $AlO_x$ covered fused silica template relative to the attraction between Structure 2 and 3 surfactants and a fused silica template. This strengthened interaction will further increase the surfactant partition ratio, such that more surfactant remains on the template surface after the template is separated from the patterned layer.

A four point bending adhesion test was used to assess how strongly exemplary surfactants cling to a template surface during template separation. Table 2 lists three materials (Bulk Material, Priming Material A, and Priming Material B) used for adhesion testing as listed by weight (grams):

TABLE 2

Materials for Imprint Lithography.

|  | Bulk Material | Priming Material A | Priming Material B |
|---|---|---|---|
| IBOA | 56 | 56 | 56 |
| Medol 10 | 19 | 19 | 19 |
| HDODA | 20 | 20 | 20 |
| Irgacure 907 | 1 | 1 | 1 |
| Darocur 4265 | 4 | 4 | 4 |
| FS2000 |  | 2 |  |
| Surfactant 2 |  |  | 2 |

IBOA (isobornyl acrylate) is available from Sartomer Company, Inc. (Exton, Pa.), under the product name SR 506. Medol 10 is an acrylate available from Osaka Organic Chemical Industry Limited (Japan). HDODA (hexanediol diacrylate) is available from Cytec Industries Inc. (Woodland Park, N.J.). Irgacure 907 and Darocur 4265 are photoinitiators available from Ciba Specialty Chemicals (Tarrytown, N.Y.). MASURF FS-2000 is an example of a Structure 1 surfactant. Surfactant 2 is shown in FIG. 8 as Structure 2.

A four-point bending fixture (not shown) was adopted for the adhesion test and technique, similar to that described in "Measurement of Adhesive Force Between Mold and Photo-curable Resin in Imprint Technology" Japanese Journal of Applied Physics, 41 (2002): 4194-4197, which is incorporated by reference herein. Each adhesion test involved two glass slides laid crosswise. Each glass slide was approximately 1 mm thick, and 75×25 mm in the lateral dimension.

The bottom glass slide was coated with an adhesion layer. The adhesion layer, described in U.S. Patent Publication No. 2007/0021520, which is incorporated by reference herein, was formed from a mixture of approximately 77 g of IsoRad 501, 22 g of Cymel 303ULF, 1 g of Cycat 4040, and 1900 g of PM Acetate. Both the Cymel 303ULF (cross-linking agent) and Cycat 4040 (catalyst) are available from Cytec Industries, Inc. (West Patterson, N.J.). One of the main components of Cymel 303ULF is hexamethoxymethyl-melamine (HMMM). The methoxyl functional groups of HMMM can participate in many condensation reactions. IsoRad 501 is an aromatic compound available from Schenectady International, Inc. (Schenectady, N.Y.). IsoRad 501, Cymel 303ULF, and Cycat are combined and then introduced into approximately 1900 grams of PM Acetate, a solvent consisting of 2-(1-methoxy) propyl acetate sold by Eastman Chemical Company (Kingsport, Tenn.).

The adhesion layer was cured at 160° C. for 4 minutes on a hot plate. For each set of adhesion tests, a fresh adhesion layer coated bottom glass slide was used. The top glass slide (fused silica) was re-used to probe how strongly the surfactant clung to the template surface.

For the baseline adhesion test, droplets of fluid bulk imprinting material were disposed on an adhesion layer coated glass slide. The second fused silica slide was laid in a crosswise direction on top of the imprinting material. The polymerizable imprinting bulk material was subsequently cured. A four-point bending compression force was applied to separate the slides. The maximum force/load was taken as the adhesion strength or value. The beam distance of the top and bottom two points was 60 mm, and the load was applied at the speed of 0.5 mm per minute.

To test how strongly a surfactant clung to a fused silica surface during separation, droplets of priming material A were disposed on an adhesion layer coated glass slide, then the second fused silica slide was laid crosswise on the top. The priming material A was subsequently cured. A four-point bending compression force was applied to separate the slides. After the separation, the top fused silica slide was kept for further testing. The top fused silica retained some MASURF® FS-2000 from this priming step. To test how much release agent remained on fused silica surface after separation, the same slide was re-tested with bulk imprinting material again in the same four point bending set-up. The maximum force/load was taken as the adhesion value. Comparing the adhesion value of the first separation to the second and successive separations provided a qualitative gauge of the interaction strength between the Structure 1 surfactant and the fused silica surface.

To test how strongly the Structure 2 surfactant interacts with the fused silica surface during separation, droplets of priming material B were disposed on an adhesion layer coated glass slide, and the second fused silica slide was laid crosswise on the top. The priming material B was subsequently cured. A four-point bending compression force was applied to separate the slides. After the separation, the top fused silica slide was kept for further testing. The top fused silica retained Structure 2 surfactant from this priming step. To test how much surfactant remained on the fused silica surface after separation, the same slide was re-tested with bulk imprinting material again in the same four point bending set-up. The maximum force/load was taken as the adhesion value. By comparing the adhesion value for priming material B with the adhesion values for the bulk material and the priming material A, a qualitative assessment of interaction strength between the Structure 2 surfactant and the fused silica surface was made.

The baseline adhesion, or for the bulk material without an a priori release layer and without any surfactant or release agent, shows an adhesion strength of 3.0 lbf. A typical adhesion strength with full surfactant coverage is about 0.8 to 1.0 lbf. Test results for priming materials A and B are shown in Table 3.

TABLE 3

Adhesion tests with Structure 1 and 2 Surfactants

| Fused silica slide treated with priming material, then tested with bulk material | Priming Material A | Priming Material B |
|---|---|---|
| $1^{st}$ test | 1.6 lbf | 0.8 lbf |
| $2^{nd}$ test (same fused silica slide re-used) | 2.2 lbf | 1.2 lbf |
| $3^{rd}$ test (same fused silica slide re-used) |  | 1.2 lbf |
| $4^{th}$ test (same fused silica slide re-used) |  | 1.0 lbf |
| $5^{th}$ test (same fused silica slide re-used) |  | 1.0 lbf |
| $6^{th}$ test (same fused silica slide re-used) |  | 1.2 lbf |
| $7^{th}$ test (same fused silica slide re-used) |  | 1.1 lbf |
| $8^{th}$ test (same fused silica slide re-used) |  | 1.0 lbf |
| $9^{th}$ test (same fused silica slide re-used) |  | 2.2 lbf |

Table 3 shows that the surfactant priming effect (reducing adhesion strength of the glass slides) lasts much longer in the case of the Structure 2 surfactant than in the case of Structure 1 type surfactant (MASURF® FS-2000). This illustrates that the Structure 2 surfactant clings to the fused silica template through stronger forces or interactions than the Structure 1 surfactant and is able to overcome the pull force of the solidified resist much better than MASURF® FS-2000. In other words, the Structure 2 surfactant has a stronger affinity for (e.g., stronger polar interactions with) a fused silica template than MASURF® FS-2000. The stronger interactions or affinity in the case of the Structure 2 surfactant may be attributed at least in part to the stronger polar interactions (e.g. hydrogen bonding interactions) per surfactant molecule of the cyclic hydrogen bonding structure in FIG. 10.

Further modifications and alternative embodiments of various aspects will be apparent to those skilled in the art in view of this description. Accordingly, this description is to be construed as illustrative only. It is to be understood that the forms shown and described herein are to be taken as examples of embodiments. Elements and materials may be substituted for those illustrated and described herein, parts and processes may be reversed, and certain features may be utilized independently, all as would be apparent to one skilled in the art after having the benefit of this description. Changes may be made in the elements described herein without departing from the spirit and scope as described in the following claims.

What is claimed is:

1. An imprint lithography release agent comprising:
   a non-polar fluorinated portion comprising a perfluorinated polyether; and
   a polar poly(oxyalkylene) portion bonded to the non-polar fluorinated portion, the polar poly(oxyalkylene) portion formed from a multiplicity of oxyalkylene units comprising at least one ethylene oxide unit.

2. The imprint lithography release agent of claim 1, wherein the multiplicity of oxyalkylene units comprises at least three ethylene oxide units.

3. The imprint lithography release agent of claim 1, wherein the multiplicity of oxyalkylene units comprises at least one propylene oxide unit.

4. The imprint lithography release agent of claim 3, wherein the multiplicity of oxyalkylene units comprises at least three propylene oxide units.

5. The imprint lithography release agent of claim 1, the release agent having the chemical structure

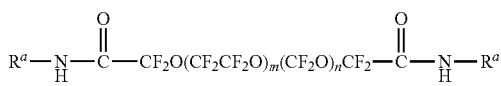

wherein each $R^a$ is independently $H_3C[OCH_2CH_2]_x[OCH_2CHCH_3]_y$, and m, n, x, and y are integers.

6. An imprint lithography release agent comprising:
a non-polar fluorinated portion comprising a perfluorinated polyether; and
a polar portion bonded to the non-polar fluorinated portion, wherein the polar portion forms polar interactions with a surface comprising oxygen.

7. The imprint lithography release agent of claim 6, wherein the polar portion comprises a carboxyl group.

8. The imprint lithography release agent of claim 6, wherein the polar portion comprises two or more hydroxyl groups.

9. The imprint lithography release agent of claim 6, wherein the polar portion comprises a nitrogen atom.

10. The imprint lithography release agent of claim 9, wherein nitrogen atom is part of a heterocycle.

11. The imprint lithography release agent of claim 9, wherein the polar portion comprises two nitrogen atoms.

12. The imprint lithography release agent of claim 11, wherein the polar portion comprises a pyridazinyl group.

13. The imprint lithography release agent of claim 6, wherein the polar interactions are hydrogen bonding interactions.

14. The imprint lithography release agent of claim 6, wherein the polar interactions form a cyclic structure at the surface.

15. The imprint lithography release agent of claim 6, wherein the release agent forms a covalent bond with the surface, and the strength of the covalent bond is less than the strength of a silicon-oxygen bond at the surface.

16. The imprint lithography release agent of claim 15, wherein the release agent comprises a boron atom, and the covalent bond is formed between the boron atom and the surface.

17. The imprint lithography release agent of claim 6, the release agent having the chemical structure

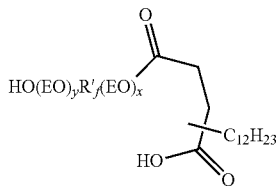

or a derivative thereof, wherein $R_f'$ is

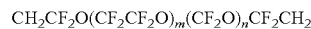

and m, n, x, and y are integers.

18. The imprint lithography release agent of claim 6, having the chemical structure

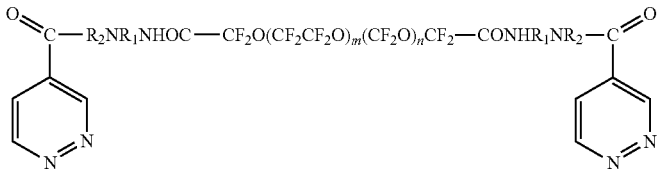

wherein m and n are integers and $R_1$ and $R_2$ are carbon-containing.

19. A imprint lithography liquid resist comprising:
a monomer;
a cross-linking agent;
a photoinitiator;
a catalyst; and
a release agent comprising:
a non-polar fluorinated portion comprising a perfluorinated polyether; and
a polar poly(oxyalkylene) portion bonded to the non-polar fluorinated portion, the polar poly(oxyalkylene) portion formed from a multiplicity of oxyalkylene units comprising at least one ethylene oxide unit.

20. The liquid resist of claim 19, wherein the multiplicity of oxyalkylene units comprises at least one propylene oxide unit.

21. The liquid resist of claim 19, further comprising a compound comprising a perfluorinated polyether group and one or more acrylate groups.

22. The liquid resist of claim 21, wherein the compound comprising the perfluorinated polyether group and the one or more acrylate groups has the chemical structure

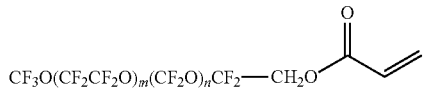

wherein m and n are integers.

23. The liquid resist of claim 21, wherein the compound comprising the perfluorinated polyether group and the one or more acrylate groups has the chemical structure

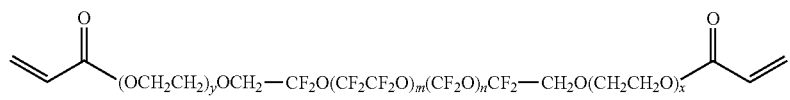
wherein m, n, x, and y are integers.